United States Patent [19]

Quadbeck-Seeger et al.

[11] 4,020,102
[45] Apr. 26, 1977

[54] PRODUCTION OF 2-HYDROXYNAPHTHALENE-3-CARBOXYLIC ACID

[75] Inventors: Hans-Juergen Quadbeck-Seeger, Bad Duerkheim; Helmut Hoch, Wachenheim, both of Germany

[73] Assignee: BASF Aktiengesellschaft, Ludwigshafen (Rhine), Germany

[22] Filed: Sept. 25, 1975

[21] Appl. No.: 616,684

[30] Foreign Application Priority Data

Oct. 19, 1974 Germany .......................... 2449779

[52] U.S. Cl. .............................. 260/520 A; 260/525
[51] Int. Cl.² ................... C07C 51/15; C07C 51/48
[58] Field of Search ...................... 260/520 A, 525

[56] References Cited

UNITED STATES PATENTS

| 2,824,892 | 2/1958 | Barkley | 260/520 A |
| 3,405,169 | 10/1968 | Leug et al. | 260/520 A |
| 3,405,170 | 10/1968 | Leug et al. | 260/520 A |
| 3,655,744 | 4/1972 | Yasuhara et al. | 260/520 A |

Primary Examiner—Norman Morgenstern
Attorney, Agent, or Firm—Johnston, Keil, Thompson & Shurtleff

[57] ABSTRACT

2-Hydroxynaphthalene-3-carboxylic acid is prepared by the reaction of sodium-β-naphtholate with carbon dioxide, extraction of the reaction mixture in the presence of water with benzene or a benzene derivative in a specific ratio and separation of the end product from the extracted mixture. The product is a starting material for the production of dyes and a coupling component in the manufacture of azo dyes.

22 Claims, No Drawings

PRODUCTION OF 2-HYDROXYNAPHTHALENE-3-CARBOXYLIC ACID

The invention relates to a process for the production of 2-hydroxynaphthalene-3-carboxylic acid by reaction of sodium-β-naphtholate with carbon dioxide, extraction of the reaction mixture in the presence of water with benzene or a derivative of benzene in a specific ratio and separation of the end product from the extracted mixture.

A well-known method for the production of 2-hydroxynaphthalene-3-carboxylic acid from β-naphthol consists in converting the β-naphthol by reaction with caustic soda solution into a sodium salt and then reacting the sodium salt with carbon dioxide at elevated temperature and superatmospheric pressure to form the disodium salt of 2-hydroxynaphthalene-3-carboxylic acid (BIOS Report No. 986, pages 234 et seq.; Ullmanns Encyklopadie der technischen Chemie, volume 12, pages 606 et seq.). 2-Hydroxynaphthalene-3-carboxylic acid is a valuable starting material for the production of dyes and a coupling component fo the manufacture of azo dyes.

For the said purposes a very pure end product has to be used because impurities in the dyes seriously interfere with tinctorial behavior. In the said method not only is β-naphthol obtained but also a high proportion of byproducts in the form of condensation products and resinuous polymers of β-naphthol may be observed. Similarly during the production of the 3-carboxylic acid the intermediately formed 2-hydroxynaphthalene-1-carboxylic acid may be rearranged into dibenzoxanthone and thus the naphthol on which it is based is withdrawn from recovery or reaction to form 2-hyroxy-naphthalene-3-carboxylic acid:

The presence of β-naphthol causes an adulteration of the desired hue and a deterioration in the fastness properties because β-naphthol, like 2-hydroxynaphthalene-3-carboxylic acid, reacts as a coupling component. The resin and xanthone make the pigments prepared from the 2-hydroxynaphthalene-3-carboxylic acid turbid. Moreover for ecological reasons it is necessary to remove all these impurities as completely as possible from effluents and off-gas.

The reaction mixture is worked up in large scale operation by the following method (BIOS Report No. 986, pages 238 and 239): the reaction mixture dissolved in water is diluted to about ten times its volume, neutralized and cooled to about 10° to 20 C to precipitate β-naphthol and the byproducts: xanthone and resin. The resin settles out and the supernatant suspension of β-naphthol is filtered off through a filter press. The large volume of aqueous mother liquor which contains the disodium salt of 2-hydroxynaphthalene-3-carboxylic acid thereafter has to be heated again to 80° C and the 2-hydroxynaphthalene-3-carboxylic acid has to be precipitated therefrom by acidification and separated.

The working up procedure, which ideally should be simple, continuous and easy to monitor and control, is expensive and protracted. Large volumes of materials have to be transported, filtered, cooled and heated up. The β-naphthol separated has to be processed in separate steps. For example the moist filter cakes are transferred to a dehydration vessel where the mixture is melted, dehydrated and then distilled.

The object of the present invention is to provide a novel process for producing 2-hydroxynaphthalene-3-carboxylic acid in a simpler and more economical way in a good yield and better purity and in a better space-time yield.

We have found that 2-hydroxynaphthalene-3-carboxylic acid is advantageously obtained in a method of reacting sodium β-naphtholate with carbon dioxide at elevated temperature and separating the end product from the reaction mixture by extracting the reaction mixture in the presence of at least 15 moles of water per mole of starting naphtholate a pH of from 4 to 8 and at a temperature of from 30° to 120° C with a phenyl compound of the formula (I):

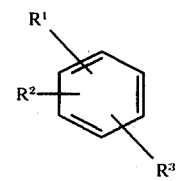

(I)

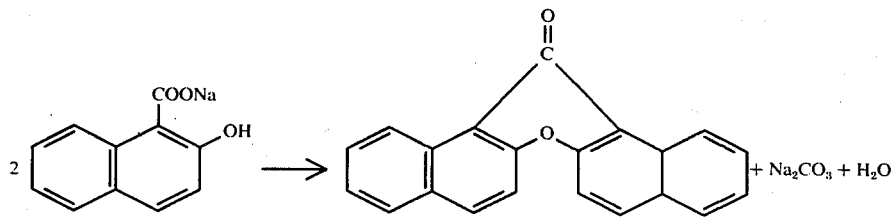

in which $R^1$, $R^2$ and $R^3$ are identical or different and each is hydrogen, an aliphatic radical or halogen, in a ratio of from 0.2 to 1.8 moles of the phenyl compound (I) per mole of starting naphthol and separating the end product from the extracted mixture by a conventional method.

The reaction may be represented by the following equations:

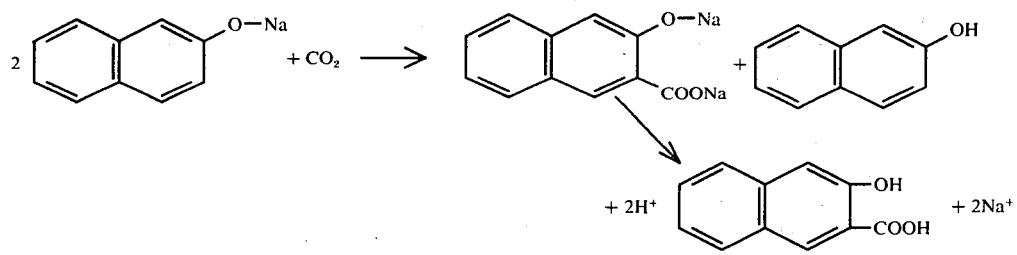

As compared with prior art methods the process according to the invention gives 2-hydroxynaphthalene-3-carboxylic acid in good yields and better purity and (by reason of the more rapid working up) in better space-time yields in a simpler and more economical way. The process is more acceptable ecologically and the operation of the plant, particularly on an industrial scale, is safer and simpler. The byproducts formed such as xanthone, condensation products of β-naphthol or highly polymerized resins are separated more rapidly and more completely from the end product.

All these advantageous results are surprising having regard to the prior art. It was not to be expected that the solvents according to this invention in the presence of a small amount of water or of concentrated aqueous solutions or suspensions of the reaction mixture would dissolve more than twice the weight of β-naphthol and substantially larger amounts of xanthone and resin than correspond to their maximum solubilities for these substances at the same temperature. For example solubilities of β-naphthol in the solvents according to the invention in the presence of water at temperatures of from 80° to 90° C are in the range of from 60 to 90% by weight of β-naphthol. It is moreover surprising that unlike the byproducts of similar constitution, the end product itself does not dissolve to any significant extent in the solvent according to the invention and the presence of water or the solution or suspension of the end product in the reaction mixture does not increase this solubility in the extractant according to the invention but even decreases it. The following Tables 1 and 2 illustrate the advantages of the process according to the invention.

Table 1

Solubility of β-naphthol in various solvents at 80° C:

| Solvent (parts) | amount of β-naphthol dissolved (parts) | (% by weight) |
| --- | --- | --- |
| xylene (89) | 35 | 28.2 |
| toluene (100) | 62 | 38.3 |
| chlorobenzene (50) | 30 | 37.5 |
| dichlorobenzene (50) | 21 | 29.6 |
| benzene (50) | 35 | 41.0 |

Table 2

Solubility of β-naphthol in various solvents in the presence of water at 80° C:

| Solvent (parts) | water (parts) | amount of β-naphthol dissolved (parts) | (% by weight) |
| --- | --- | --- | --- |
| technical xylene (89) | 50 | 180 | 67 |
| toluene (100) | 50 | 314 | 76 |
| chlorobenzene (50) | 20 | 123 | 71 |
| dichlorobenzene (50) | 20 | 111 | 69 |
| benzene (50) | 10 | 73 | 60 |

Resins, condensation products of naphthol and dibenzoxanthone are extracted in a similar manner. The byproducts may thus be separated optimally with small amounts of water and extractant.

The naphtholates may be used as pure substances for carrying out the reaction; it is convenient however to combine the production of the naphtholates and the reaction, thus carrying out a three-stage process in a single reactor. The naphtholates may be prepared by a known method of producing naphthol using sodium compounds or potassium compounds such as sodium carbonate, potassium carbonate, potassium hydroxide or sodium hydroxide for the salt formation (Ullmanns Encyklopadie der technischen Chemie, volume 12, pages 603 and 604). It is convenient to dissolve the β-naphthol in caustic soda solution, alone or mixed with caustic potash solution. The solution or suspension of β-naphtholate obtained in this way is dehydrated by heating and used immediately for the carboxylation reaction. Production of the naphtholate may be carried out at atmospheric or superatmospheric pressure, continuously or batchwise. The mixture from the sodium naphtholate production fed to the first stage of the reaction according to the invention advantageously contains a total amount of sodium (calculated as sodium hydroxide) which is the stoichiometric amount based on the total naphthol in the mixture. If desired an excess of naphthol above the stoichiometric amount, for example up to about 10% by weight, based on the total amount of sodium (calculated as sodium hydroxide) may be present in the starting mixture. It is also possible to heat to the reaction temperature β-naphthol and aqueous caustic soda solution, in the presence or absence of an inert gas such as nitrogen.

In the case of naphtholate mixture, the two naphtholates may be prepared separately from one another by the said methods and the resultant reaction mixtures combined; it is generally more convenient however to prepare the naphtholate mixture in a common reaction. In the case of mixtures of alkali metal naphtholates there are generally used from 0.02 to 0.5 and preferably from 0.02 to 0.2 mole of potassium β-naphtholate per mole of sodium β- naphtholate and therefore for the production of the starting materials it is convenient to choose molar ratios of potassium hydroxide to sodium hydroxide of from 0.02:1 to 0.5:1 and preferably from 0.02:1 to 0.2:1. The production of the naphtholate may be carried out at atmospheric or superatmospheric pressure and continuously or batchwise. The mixture from the naphtholate production supplied to the first stage of the reaction according to the invention advantageously contains a total amount of sodium and potassium (calculated as sodium hydroxide and potassium hydroxide) which is the stoichiometric amount in relation to the total naphthol in the mixture. An excess of naphthol, for example of up to 10% by weight, above the stoichiometric amount may also be present based on the total amount of alkali (calculated as alkali metal hydroxide) in the starting mixture. β-naphthol and aqueous caustic alkali solution may also be heated to the reaction temperature, if desired in the presence of an inert gas such as nitrogen.

In the first stage of the reaction the starting mixture is advantageously heated to a temperature of at least 180° C, preferably to from 200° to 280° C and particularly to from 240° to 265° C, at atmospheric or superatmospheric pressure and continuously or batchwise. The second stage of the reaction, the carboxylation, is advantageously also carried out under these conditions of temperature and pressure and continuously or batchwise. During the heating of the starting mixture, for example for 30 to 60 minutes, water distils off. The carboxylation is conveniently carried out at superatmospheric pressure, preferably at a pressure of from 2 to 50 atmospheres and particularly from 3 to 10 atmospheres, and with an amount of carbon dioxide of from 0.5 to 10 moles and preferably from 0.5 to 2 moles for each mole of naphtholate. The reaction period for the carboxylation is conveniently from one hour to four hours.

The production of the 2-hydroxynaphthalene-3-carboxylic acid may also be carried out by the method described in the BIOS Report or Ullmanns Encyklopadie mentioned above. Production may also be carried out in the presence of an inhibitor, for example according to the method described in German Pat. application P 24 07 114.5, or in the presence of an araliphatic compound containing at least two aromatic radicals joined together by a cycloaliphatic and/or aliphatic radical by the method described in German Laid-Open Specification (DOS) No. 2,260,637.

Any of a wide range of processing methods are possible after the carboxylation is over. For example the mixture may be cooled and the suspension of the disodium salt of 2-hydroxy-3-naphthoic acid introduced into water or the major portion or all of the β-naphthol may be distilled off in vacuo and the residue dissolved with water at from about 90° to 100° C. The β-naphthol may also be extracted from the reaction mixture (stripped) with the stream of carbon dioxide which is conveniently recycled. For example carbon dioxide may be forced into the melt until the absorption of carbon dioxide subsides. Then by applying a vacuum the liberated β-naphthol is distilled off and the melt which remains is carboxylated again. These operations are repeated until carbon dioxide is no longer absorbed and β-naphthol no longer distils over; this is usually the case after from two to four carboxylations alternating with from two to three distillations of the β-naphthol formed.

The reaction mixture may also be cooled and, when one of the said polynuclear araliphatic compounds is used which has a boiling point similar to that of naphthol, the araliphatic compound and the major portion or all of the β-naphthol distilled off in vacuo and the residue dissolved with water at from about 90° to 100° C. When for example methylphenylindan is used, the solvent may also be distilled off in vacuo after the end of the carboxylation reaction and the suspension of the disodium salt of 2-hydroxynaphthalene-3-carboxylic acid which remains is stirred with water or poured into water.

In a preferred embodiment no organic solvent is used in the reaction and the unreacted β-naphthol is not removed by distillation or only partly removed by distillation at the end of the reaction. Instead the reaction mixture is advantageously cooled to the reaction temperature and made into a suspension with water. At least 15 moles, especially from 25 to 60 moles and preferably from 30 to 40 moles of water is used per mole of starting naphtholate in the extraction and expediently for suspending the reaction mixtue. Extraction temperatures of from 30° to 120° C, preferably from 60° to 100° C and particularly from 75° to 90° C are used. Extraction is carried out with the extractant of formula (I) in an amount of from 0.2 to 1.8 moles and preferably from 0.8 to 1.2 moles of benzene (I) per mole of starting naphtholate. Preferred extractants include benzenes (I) in whose formula $R^1$, $R^2$ and $R^3$ are identical or different and each is hydrogen, alkyl of one to six and preferably one, two or three carbon atoms, or bromine or preferably chlorine. Benzenes (I) having one or two substituents are particularly advantageous, preferably o-chlorotoluene, m-chlorotoluene, p-chlorotoluene, o-bromotoluene, m-bromotoluene, p-bromotoluene, ethylbenzene, isopropylbenzene, fluorobenzene, iodobenzene, bromobenzene, o-dibromobenzene, m-dibromobenzene, p-dibromobenzene, 1,2,4-trichlorobenzene, o-diethylbenzene, m-diethylbenzene, p-diethylbenzene, n-propylbenzene, n-butylbenzene, tert.-butylbenzene, isobutylbenzene, pentylbenzene, hexylbenzene, 1,2,4-trimethylbenzene, 1,2,4-triethylbenzene, 2,4-dichlorotoluene, benzene and particularly toluene, o-xylene, m-xylene, p-xylene, chlorobenzene, p-dichlorobenzene, m-dichlorobenzene and p-dichlorobenzene. Prior to the extraction the aqueous reaction mixture, which after suspension may if desired be diluted with more water within the abovementioned amounts, has its pH adjusted to from 4 to 8, preferably from 5 to 7 and particularly from 5 to 6, for example by adding a mineral acid such as hydrochloric acid.

When some of the β-naphthol, for example from 40 and 80% by weight of the total amount of β-naphthol present in the reaction mixture, is distilled off prior to the extraction it is advantageous to select for the extraction an amount of water in the reaction mixture of from 25 to 40 moles and an amount of benzene (I) of from 0.8 to 0.2 mole per mole of starting naphtholate. It is easy to determine the amount of naphthol in relation to resin and xanthone in the reaction mixture by a preliminary experiment and to adjust the amounts of water and benzene (I) for the extraction accordingly. It is preferred to use from 25 to 50 moles and particularly from 30 to 40 moles of water and from 0.2 to 1.8 and particularly from 0.4 to 0.6 mole of benzene (I) per mole of β-naphthol, from 25 to 50 moles and particularly 30 to 40 moles of water and from 5 to 50 moles and particularly from 10 to 20 moles of benzene (I) per mole of xanthone and from 1000 to 6000% and particularly from 3000 to 4000% by weight of water and from 100 to 1000% and particularly from 200 to 400% by weight of benzene (I) based on the weight of resin and condensation products of the naphthol.

The extraction is generally carried out for from one minute to fifteen minutes at atmospheric or superatmospheric pressure, continuously or batchwise. Examples of extraction apparatus which may be used include spray columns, sieve plate columns, packed columns, columns having moving or rotating baffles, rotating disc extractors, Graeser contactors, separating columns, pulse columns, vibrating cylinders, mixer-separator batteries, mixer-separator towers, basket extractors, centrifugal extractors and perforated-bottom extractors. β-Naphthol and solvent are conveniently separated by distillation from the extract which contains β-naphthol, resin and xanthone, while the resin and xanthone remain in the bottoms. Loss of solvent is low and the β-naphthol which is recovered almost completely may be immediately used again in the reaction.

Acid is preferably added again to the aqueous extracted mixture to obtain the free carboxylic acid; it is possible within a wide range to use any acid or method for the conversion of a salt into the corresponding acid. The aqueous phase freed from β-naphthol is conveniently acidified at a temperature of from 50° to 100° C, preferably from 70° to 90° C and particularly from 75° to 85° C, advantageously with aqueous hydrochloric acid, for example of from 5 to 35% by weight strength, to a pH of less than 4 and preferably of from 3 to 4, stirred for from five to fifteen minutes, then cooled for example to 50° C and suction filtered. Slight contamination of the 2-hydroxynaphthalene-3-carboxylic acid with 2-hydroxynaphthalene-6-carboxylic acid may be easily separated making use of the far better solubility of the latter in hot water. The isomers may also be separated from the waste aqueous liquor by cooling.

2-Hydroxynaphthalene-3-carboxylic acid which can be prepared by the process according to the invention is a valuable starting material for the production of dyes and a coupling component for the manufacture of azo dyes. The abovementioned publication and particularly the standard work of Ullmann, volume 12, page 609, may be referred to for details of uses.

The invention is illustrated in the following Examples in which the parts specified are parts by weight.

EXAMPLE 1

A stirred autoclave is charged with 1220 parts of β-naphthol, 608 parts of aqueous caustic soda solution (50% by weight) and 27 parts of aqueous caustic potash solution (85% by weight). The mixture is well mixed under nitrogen, heated to an internal temperature of 260° C and kept for 30 minutes at this temperature. The dehydration is then practically complete. Carboxylation is carried on for 3 hours at a temperature of 260° C with dry carbon dioxide at a pressure of 7 atmospheres. The absorption of $CO_2$ is monitored by a gas meter. After the absorption is ended 350 parts of β-naphthol is distilled off at 20 mm of Hg and then in the manner above described carbon dioxide is again forced in and the mixture carboxylated for 2 hours. A total of 300 parts of carbon dioxide is absorbed in a carboxylation period of 300 minutes. The reaction mixture is stirred with 5000 parts of water and dissolved. The solution is cooled to 80° to 90° C, acidified with 50% by weight sulfuric acid to a pH of 6.5 and then extracted for fifteen minutes with a total of 800 parts of a mixture of m-xylene and p-xylene in the ratio 2.3:1. The phases are then separated and the aqueous phase is acidified to a pH of 3 at 90° C with 50% by weight sulfuric acid. The precipitated 2-hydroxynaphthalene-3-carboxylic acid is separated by filtration from the hot solution at 80° C. 530 parts of 2-hydroxynaphthalene-3-carboxylic acid is obtained. This is 73% of theory based on reacted naphtholate deducting the β-naphthol obtained. It contains 99% by weight of 2-hyroxynaphthalene-3-carboxylic acid and 0.5% by weight of β-naphthol. The melting point is 218° to 220° C.

The xylene extraction phase is distilled in vacuo at 12 mm. 780 parts of xylene and 325 parts of β-naphthol (boiling point 155° C at 12 mm) are obtained. 130 parts of resin and xanthones remain as distillation residue.

EXAMPLE 2

A sodium β-naphtholate obtained by dehydration of a mixture of 1220 parts of β-naphthol and 640 parts of aqueous caustic soda solution (50% by weight) is carboxylated as described in Example 1 and 455 parts of β-naphthol is distilled off. The reaction mixture is dissolved in 5000 parts of water. The solution is cooled to 80° C, acidified with 50% by weight sulfuric acid to a pH of 6.5 and then extracted with 750 parts of toluene for 15 minutes. The two phases are separated. The aqueous phase is adjusted to a pH of 3 at 90° C with 50% by weight sulfuric acid and the 2-hydroxynaphthalene-3-carboxylic acid precipitated is separated by filtering the hot 80° C solution. 542 parts of 2-hydroxynaphthalene-3-carboxylic acid (72% of theory based on reacted naphtholate deducting the β-naphthol obtained) is obtained having a content of 99% by weight and a β-naphthol content of 0.4% by weight and a melting point of 217° to 221° C.

The toluene extract is distilled. 730 parts of toluene and 195 parts of β-naphthol are obtained. Resin and xanthone remain as the distillation residue.

EXAMPLE 3

The reaction is carried out as described in Example 2. After the solution of the reaction mixture in 5000 parts of water the solution is cooled to 85° C, acidified with 50% by weight sulfuric acid to a pH of 6.5 and then extracted for 15 minutes with a total of 900 parts of chlorobenzene. After separation of the phases the further working up is carried out as described in Example 2. 540 parts of 2-hydroxynaphthalene-3-carboxylic acid is obtained (72% of theory based on reacted naphtholate deducting the β-naphthol obtained) with a content of 99% by weight, a β-naphthol content of 0.5% by weight and a melting point of from 217° to 220° C.

The chlorobenzene extract is distilled. 860 parts of chlorobenzene and 193 parts of β-naphthol are obtained.

EXAMPLE 4

The reaction is carried out analogously to Example 1. The solution of the reaction mixture cooled to 85° C is acidified to a pH of 6.5 with 50% by weight sulfuric acid and then extracted for fifteen minutes with a total of 900 parts of n-propylbenzene. After separation of the phases they are further processed as described in Example 1.

520 parts of 2-hydroxynaphthalene-3-carboxylic acid (75% of theory based on reacted naphtholate less the β-naphthol obtained) is obtained with a content of 99% by weight and a β-naphthol content of 0.5% by weight. The melting point is 217° to 221° C.

The n-propylbenzene extract is distilled in vacuo (100 mm). 850 parts of n-propylbenzene and 320 parts of β-naphthol are obtained. 140 parts of resin and xanthone are obtained as the distillation residue.

We claim:

1. A process for the manufacture of 2-hydroxynaphthalene-3-carboxylic acid which comprises reacting sodium β-naphtholate or a mixture of sodium β-naphtholate and 0.02 to 0.5 mol, per mol of sodium β-naphtholate, of potassium β-naphtholate with carbon dioxide at a temperature of at least 180° C and at a pressure of 2 to 50 atmospheres in the absence of an organic solvent, and extracting β-naphthol, xanthone, and resins and/or condensation products of naphthol from the reaction mixture in the presence of at least 15 moles of water per mole of starting naphtholate at a pH of from 4 to 8 and at a temperature of from 30° to 120° C with a phenyl compound of the formula (I):

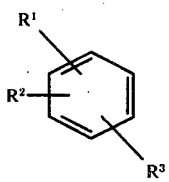

in which
R¹, R² and R³ are identical or different and each is a hydrogen atom, alkyl of 1 to 6 carbon atoms or a halogen atom, in a ratio of from 0.2 to 1.8 moles of phenyl compound (I) per mole of starting naphtholate and recovering 2-hydroxynaphthalene-3-carboxylic acid from the aqueous phase of the extraction step.

2. A process as claimed in claim 1, wherein the reaction is carried out with said mixture of potassium β-naphtholate and sodium β-naphtholate.

3. A process as claimed in claim 1, wherein the reaction is carried out at a temperature of from 200° to 280° C.

4. A process as claimed in claim 1, wherein the reaction is carried out at a temperature of from 240° to 265° C.

5. A process as claimed in claim 1, wherein the carboxylation reaction is carried out at a pressure of from 3 to 10 atmospheres and with an amount of carbon dioxide of from 0.5 mole to 10 moles per mole of naphtholate.

6. A process as claimed in claim 1, wherein the extraction is carried out with from 25 to 60 moles of water to 1 mole of starting naphtholate.

7. A process as claimed in claim 1 wherein the extraction is carried out at temperature of from 60° to 100° C.

8. A process as claimed in claim 1, wherein the extraction is carried out at from 75° to 90° C.

9. A process as claimed in claim 1, wherein the extraction is carried out with from 0.8 mole to 1.2 moles of phenyl compound (I) per mole of starting naphtholate.

10. A process as claimed in claim 1, wherein the extraction is carried out with o-chlorotoluene, m-chlorotoluene, p-chlorotoluene, o-bromotoluene, m-bromotoluene, p-bromotoluene, ethylbenzene, isopropylbenzene, fluorobenzene, iodobenzene, bromobenzene, o-dibromobenzene, m-dibromobenzene, p-dibromobenzene, 1,2,4-trichlorobenzene, o-diethylbenzene, m-diethylbenzene, p-diethylbenzene, n-propylbenzene, n-butylbenzene, tert.-butylbenzene, isobutylbenzene, pentylbenzene, hexylbenzene, 1,2,4-trimethylbenzene, 1,2,4-triethylbenzene, 2,4-dichlorotoluene, benzene, toluene, o-xylene, m-xylene, p-xylene, chlorobenzene, o-dichlorbenzene, m-dichlorobenzene or p-dichlorobenzene.

11. A process as claimed in claim 1, wherein the extraction is carried out at a pH of from 5 to 7.

12. A process as claimed in claim 1, wherein the extraction is carried out with from 25 to 50 moles of water and from 0.2 mole to 1.8 moles of phenyl compound (I) per mole of β-naphtholate, from 25 to 50 moles of water and from 5 to 50 moles of phenyl compound (I) per mole of xanthone and from 1000 to 6000% by weight of water and from 100 to 1000% by weight of phenyl compound (I) based on the weight of resin and/or condensation products of naphthol.

13. A process as claimed in claim 1, wherein the aqueous phase of the extraction step is acidified to a pH of from 3 to 4 at a temperature of from 50° to 100° C with aqueous hydrochloric acid of from 5 to 35% by weight strength, stirred for from five to fifteen minutes and then cooled to precipitate 2-hydroxynaphthalene-3-carboxylic acid.

14. A process for the manufacture of 2-hydroxynaphthalene-3-carboxylic acid derived through carboxylation of an alkali metal β-naphtholate, wherein the alkali metal consists of sodium or both sodium and potassium, to produce a reaction mixture containing the di-alkali metal salt 2-hydroxynaphthalene-3-carboxylic acid, wherein the alkali metal consists of sodium or both sodium and potassium, β-naphthol, xanthone, and resins and/or condensation products of naphthol, which comprise extracting β-naphthol, xanthone and said resins and/or condensation products in the presence of at least 15 moles of water per mole of starting alkali metal naphtholate at a pH of from 4 to 8 and at a temperature of from 30° to 120° C with a phenyl compound of the formula (I):

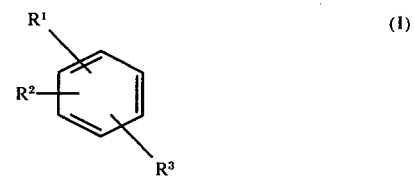

in which
R¹, R² and R³ are identical or different and each is a hydrogen atom, alkyl of 1 to 6 carbon atoms or a halogen atom, in a ratio of from 0.2 to 1.8 moles of phenyl compound (I) per mole of starting naphtholate, and recovering 2-hydroxynaphthalene-3-carboxylic acid from the aqueous phase of the extraction step.

15. A process as claimed in claim 14, wherein the extraction is carried out with from 25 to 60 moles of water to 1 mole of starting naphtholate.

16. A process as claimed in claim 14, wherein the extraction is carried out at a temperature of from 60° to 100° C.

17. A process as claimed in claim 14, wherein the extraction is carried out at from 75° to 90° C.

18. A process as claimed in claim 14, wherein the extraction is carried out with from 0.8 mole to 1.2 moles of phenyl compound (I) per mole of starting naphtholate.

19. A process as claimed in claim 14, wherein the extraction is carried out with o-chlorotoluene, m- chlorotoluene, p-chlorotoluene, o-bromotoluene, m-bromotoluene, p-bromotoluene, ethylbenzene, isopropylbenzene, fluorobenzene, iodobenzene, bromobenzene, o-dibromobenzene, m-dibromobenzene, p-dibromobenzene, 1,2,4-trichlorobenzene, o-diethylbenzene, m-diethylbenzene, p-diethylbenzene, n-propylbenzene, n-butylbenzene, tert.-butylbenzene, isobutylbenzene, pentylbenzene, hexylbenzene, 1,2,4-trimethylbenzene, 1,2,4-triethylbenzene, 2,4-dichlorotoluene, benzene, toluene, o-xylene, m-xylene, p-xylene, chlorobenzene, o-dichlorobenzene, m-dichlorobenzene or p-dichlorobenzene.

20. A process as claimed in claim 14, wherein the extraction is carried out at a pH of from 5 to 7.

21. A process as claimed in claim 1, wherein the extraction is carried out with from 25 to 50 moles of water and from 0.2 mole to 1.8 moles of phenyl compound (I) per mole of β-naphtholate, from 25 to 50 moles of water and from 5 to 50 moles of phenyl compound (I) per mole of xanthone and from 1000 to 6000% by weight of water and from 100 to 1000% by weight of phenyl compound (I) based on the weight of resin and/or condensation products of naphthol.

22. A process as claimed in claim 14, wherein the aqueous phase of the extraction step is acidified to a pH of from 3 to 4 at a temperature of from 50° to 100° with aqueous hydrochloric acid of from 5 to 35% by weight strength, stirred for from five to fifteen minutes and then cooled to precipitate 2-hydroxynaphthalene-3-carboxylic acid.

* * * * *